(12) United States Patent
Knott et al.

(10) Patent No.: US 8,729,499 B2
(45) Date of Patent: May 20, 2014

(54) DEVICE FOR INTERNAL AND EXTERNAL STERILISATION OF PLASTIC CONTAINERS BY MEANS OF CHARGE CARRIER BEAMS

(71) Applicant: Krones AG, Neutraubling (DE)

(72) Inventors: Josef Knott, Walkenstetten/Schierling (DE); Guenter Frankenberger, Koefering (DE); Patrick Engelhard, Elsendorf (DE); Jochen Krueger, Hagelstadt (DE); Juergen Soellner, Beratzhausen (DE); Holger Mueller, Pentling (DE); Martin Watter, Regensburg (DE); Hans Scheuren, Regensburg (DE); Roland Laumer, Regensburg (DE)

(73) Assignee: Krones AG (DE)

( * ) Notice: Subject to any disclaimer, the term of this patent is extended or adjusted under 35 U.S.C. 154(b) by 0 days.

(21) Appl. No.: 13/681,061

(22) Filed: Nov. 19, 2012

(65) Prior Publication Data

US 2013/0129566 A1    May 23, 2013

(30) Foreign Application Priority Data

Nov. 21, 2011  (DE) .......................... 10 2011 055 553

(51) Int. Cl.

| | | |
|---|---|---|
| *G01N 21/00* | (2006.01) | |
| *G01N 23/00* | (2006.01) | |
| *A61N 5/00* | (2006.01) | |
| *A23C 3/07* | (2006.01) | |
| *A23B 4/16* | (2006.01) | |
| *A23L 1/31* | (2006.01) | |
| *B65B 25/06* | (2006.01) | |
| *B65D 21/06* | (2006.01) | |

(52) U.S. Cl.
CPC ... *A23B 4/16* (2013.01); *A23L 1/31* (2013.01); *B65B 25/067* (2013.01); *B65D 21/062* (2013.01); *B65D 21/066* (2013.01)

USPC .............. 250/455.11; 250/453.11; 250/492.1; 99/451

(58) Field of Classification Search
CPC .......... A23B 4/16; A23L 1/31; B65B 25/067; B65B 21/062; B65B 21/066
USPC ................ 422/1, 20, 21–22, 24, 186, 186.05, 422/186.3, 187; 250/453.11, 455.11, 492.1; 99/451; 134/1
See application file for complete search history.

(56) References Cited

U.S. PATENT DOCUMENTS

| | | | |
|---|---|---|---|
| 1,766,018 A | 6/1930 | Flook | |
| 2,660,513 A | 11/1953 | Ball | ................. 21/56 |
| 3,975,260 A | 8/1976 | Peyton et al. | ................ 209/73 |
| 4,723,392 A | 2/1988 | Takeda | ............ 53/434 |
| 5,457,939 A | 10/1995 | Bardou et al. | ................ 53/432 |
| 6,221,216 B1 | 4/2001 | Nablo et al. | ............. 204/157.15 |
| 6,354,427 B1 | 3/2002 | Pickel et al. | ............... 198/470.1 |
| 8,294,126 B2 | 10/2012 | Humele et al. | ............. 250/492.3 |
| 2005/0158218 A1 | 7/2005 | Dumargue et al. | ........... 422/121 |
| 2011/0061343 A1 | 3/2011 | Roithmeier et al. | ........... 53/452 |
| 2011/0101248 A1 | 5/2011 | Nishino et al. | ............. 250/492.3 |
| 2011/0133370 A1 | 6/2011 | Engelhard et al. | ............ 264/535 |

FOREIGN PATENT DOCUMENTS

| | | | |
|---|---|---|---|
| DE | 2527363 | 12/1976 | ................ B67C 7/00 |
| DE | 19882252 | 5/2000 | ................ A23L 3/26 |
| DE | 102008038143 | 2/2010 | ................ B29C 49/42 |
| DE | 102009041215 | 3/2011 | ................ A61L 2/18 |
| DE | 102010012569 | * 9/2011 | |
| EP | 0659683 | 12/1994 | ................ B67C 7/00 |
| EP | 1982921 | 10/2008 | ................ A61L 2/08 |
| WO | WO9707024 | 2/1997 | ................ B65B 55/04 |
| WO | WO9952810 | 10/1999 | ................ A23L 3/00 |
| WO | WO2008129397 | 10/2008 | |

OTHER PUBLICATIONS

European English translation of the Description and the Claims sections of DE 102010012569.*
German Search Report issued for corresponding application No. 10 2011 055 553.6, dated Aug. 31, 2012 (5 pgs).
International Search Report issued for corresponding application No. PCT/EP99/02193, dated Jul. 28, 1999 (3 pgs).

\* cited by examiner

*Primary Examiner* — Monzer R Chorbaji
(74) *Attorney, Agent, or Firm* — Hayes Soloway P.C.

(57) ABSTRACT

An apparatus for sterilizing at least a segment of an inner wall and a segment of an outer wall of containers by accelerated charge carriers, includes at least one first external application device for sterilizing at least a segment of an outer wall of containers and an internal application device for sterilizing at least a segment of an inner wall of containers. The internal application device at least in portions is arranged to be introduced through an opening into the container in order to apply the emitted charge carriers to an inner wall of the container. The containers are transported along a transport path during their sterilization, wherein along a segment of the transport path of the containers between the first external application device and the internal application device is arranged a pitch change device to change a distance between two containers succeeding each other along the transport path.

19 Claims, 7 Drawing Sheets

DEVICE FOR INTERNAL AND EXTERNAL STERILISATION OF PLASTIC CONTAINERS BY MEANS OF CHARGE CARRIER BEAMS

BACKGROUND OF THE INVENTION

The invention concerns an apparatus for sterilising at least a segment of an inner wall and a segment of an outer wall of containers by means of accelerated charge carriers, with at least one first external application device for sterilising at least a segment of an outer wall of containers and an internal application device for sterilising at least a segment of an inner wall of containers, wherein the internal application device at least in portions can be introduced into the container through an opening in order to apply the emitted charge carriers to an internal wall of the container, with a transport device by means of which the containers can be transported along a transport path during their sterilisation.

The invention furthermore concerns a plant for treating containers which comprises at least one device for sterilising at least a segment of an inner wall and a segment of an outer wall of containers by means of accelerated charge carriers with at least one first external application device for sterilising at least a segment of an outer wall of containers and an internal application device for sterilising at least a segment of an inner wall of containers, and a method for sterilising at least a segment of an inner wall and a segment of an outer wall of containers by means of accelerated charge carriers, wherein the container is exposed to the charge carriers from at least one first external application device for sterilising at least a segment of an outer wall of containers and an internal application device for sterilising at least a segment of an inner wall of containers, wherein the internal application device at least in portions is introduced through an opening into the container in order to apply the emitted charge carriers to an inner wall of the container, wherein the containers are transported along a transport path by means of a transport device during their sterilisation.

Sterilisation of a container to be filled is, along with the actual filling process, one of the central processing steps in aseptic filling. The possible sterilisation forms vary with regard to disinfectant and process management. However, the common factor in all is that the bactericidal effect is achieved by means of chemical processes. Thus, it is known for example to sterilise the inner wall of the containers with steam or hydrogen peroxide. Such methods are however associated with disadvantages since, because of the treatment for example with hydrogen peroxide, an escape of material can occur. To prevent these disadvantages, recent developments use ionising radiation to achieve a germ reduction. This radiation in most cases comprises accelerated electrons which are generated in a corresponding plant and conducted onto or into the container to be sterilised. The result is a reduction in or complete avoidance of the use of chemical substances, and inter alia a reduction in procurement and disposal costs.

The terms "container" and "plastic container" are used synonymously below for simplicity. These terms also include pre-products of such containers. In particular these terms relate to bottles, preferably drinks bottles but also to preforms (e.g. plastic preforms for e.g. bottles). The invention can however also be applied to other containers e.g. glass bottles.

Also the terms "disinfection" and "sterilisation", and "disinfectant" and "sterilisation agent", are used synonymously.

A clean room is a region sealed against the environment in which conditions different from the environment in relation to sterility can be maintained. In particular a clean room is a region which fulfils specific minimum requirements in relation to maximum contamination with germs. Preferably each volume part of the clean room and each of the inner surfaces of the clean room fulfils minimum requirements in relation to sterility.

Systems for sterilisation are known from the prior art which consist of an electron generating device and a bundling device. Systems are known which sterilise containers from the outside or from the inside. In internal sterilisation, charge carriers generated outside the container to be sterilised are deflected into the container to be sterilised by various e.g. mechanical or electronic elements. In this container a cloud of electrons forms which deactivates any undesirable microorganisms by interaction therewith.

An example of such a device for internal sterilisation of a container by means of electrons is described in DE 198 82 252 T1. An electron beam source is provided here which directs the radiation from the outside into the interior of the container.

Publication WO 97/07024 A discloses a method in which at least parts of the electron source can be introduced into the interior of the container. A method is described for cleaning or sterilising product packs by means of electron beams. The device disclosed in WO 97/07024 A comprises an electron gun which can be partially introduced into the interior of the container and carries accelerated electrons into the interior of a container. A stream of a gas introduced in parallel and interacting with the electron beam serves either to deflect the electron beam in the direction of the gas stream or as an aid to sterilisation by ionisation of the gas.

If no separate internal sterilisation of the containers is performed, significantly more powerful charge carrier generators are required as the accelerated charge carriers in addition must penetrate at least one outer wall of the container. Correspondingly strong shielding of the environment against the generated (scatter) radiation is necessary for such devices.

It would be particularly advantageous to be able to combine the benefits of internal sterilisation with those of separate sterilisation of the container outer wall. Such devices which can combine the benefits of the respective sterilisation method with those of the other method are not however known in the prior art. This is due in particular to the fact that the treatment times for the different sterilisations are different and the respective transport devices must therefore fulfil very different peripheral conditions.

OBJECTS OF THE INVENTION

The invention is therefore based on the object of providing an apparatus for sterilising at least a segment of an inner wall and a segment of an outer wall of containers by means of accelerated charge carriers, with separate devices for internal sterilisation and external sterilisation, which can treat a multiplicity of containers in a continuous process.

Since high cycle rates and throughput counts are achieved in particular in the plants used for production and filling of containers, a further object of the invention is to provide a corresponding plant for treating containers which includes such an apparatus for sterilising containers.

A further object of the invention is to provide a method for sterilising at least a segment of an inner wall and a segment of an outer wall of containers by means of accelerated charge carriers, with separate devices for internal sterilisation and external sterilisation, by means of which a multiplicity of containers can be treated in a continuous process.

SUMMARY OF THE INVENTION

An essential aspect of the invention is an apparatus for sterilising at least a segment of an inner wall and a segment of an outer wall of containers by means of accelerated charge carriers, with at least one first external application device for sterilising at least a segment of an outer wall of containers and an internal application device for sterilising at least a segment of an inner wall of containers, wherein the internal application device at least in portions can be introduced into the container through an opening in order to apply the emitted charge carriers to an inner wall of the container, with a transport device by means of which the containers can be transported along a transport path during their sterilisation, wherein along a segment of the transport path of the containers between the first external application device and the internal application device is arranged a pitch change device to change the distance between two containers succeeding each other along the transport path (i.e. the pitch).

With such a device it is possible to perform the internal sterilisation and external sterilisation of containers in a single common device. At the same time it is possible to design the device particularly compactly as the shielding of the environment from the radiation produced in the device can be adapted to the respective radiation occurring in the different application devices. The screening in the region of the external application device can be designed for example stronger than that in the region of the internal application device. Preferably the external application device and the internal application device are designed as separate elements and are physically separated from each other.

Preferably the external application device is located upstream of the internal application device. It would however also be conceivable for the internal application device to be arranged upstream of the external application device.

The internal application device is preferably designed in the form of a radiation finger or finger emitter which can be introduced into the interior of the container. Preferably a multiplicity of such radiation fingers are provided on a common transport device e.g. a transport star.

The arrangement of a pitch change device, to change a distance between two containers succeeding each other along the transport path, in a segment of the transport path between the first external application device and the internal application device allows the respective transport elements which transport the containers during the respective sterilisation process to be adapted independently of each other to the respective requirements. Thus for example it could be advantageous during external sterilisation for the containers to be transported in comparatively close succession. In particular for containers, in particular preforms, the distance between two containers directly succeeding each other along the transport path can be <10 cm, preferably <7.5 cm, particularly preferably <5 cm. This close arrangement is possible in particular during transport and sterilisation of preforms which have significantly smaller dimensions, in particular a smaller diameter, than finished containers. Due to the close succession of containers, e.g. preforms, the size of the gap between two directly successive containers can be minimised in the region of the external application device. As a result the proportion of charge carriers which pass through this gap unused, past the containers to be sterilised, is minimised.

Preferably by the close succession of directly adjacent containers at least in segments it is possible to reduce the speed of the individual containers along the transport path in this region and hence keep constant the number of containers transported per time interval. As a result preferably in the region of the external application device a longer treatment time is achieved which e.g. allows a rotation of the container, preferably a complete rotation of the container, along its longitudinal axis during application with the charge carrier.

In contrast, in segments greater distances between containers directly succeeding each other along the transport path can be advantageous. For example it is possible that in the region of the internal application device, greater distances are necessary between adjacent containers as the internal application device is partly introduced into the container. The internal application device here at least in portions has a diameter which allows the insertion of this portion into the interior of the container. Other portions of the internal application device such as e.g. a charge carrier generator device or a charge carrier accelerator device, a current supply device, a transformer device, a cooling device or others could also have larger dimensions independently of each other. As a result and where applicable also because of the mechanism by means of which the relative movement is achieved between the internal application device and the containers to be sterilised along their longitudinal axis, very small distances between containers directly succeeding each other along the transport path could be disadvantageous. Therefore a distance between two containers directly succeeding each other along the transport path in a segment of the transport path, preferably in the region of the internal application device, is >5 cm, preferably >7.5 cm, particularly preferably >10 cm.

An embodiment of the apparatus for sterilising containers is preferred in which the containers to be sterilised are preforms, in particular preforms for (i.e. for production of) containers for drinks and/or other fluid media. Due to the significantly smaller extension (or size, length and/or diameter) in comparison with finished containers, the preforms to have a smaller surface to be sterilised. As a result it is also possible to dimension the application devices smaller. Preferably radiation quantity, radiation intensity, acceleration voltage and/or other parameters can be improved so that the energy requirements of the device and/or the production and/or procurement costs can be reduced.

An embodiment of the apparatus for sterilising containers is preferred in which the transport path is curved at least in one segment in which is arranged the first external application device for sterilising at least a segment of an outer wall of containers. With this embodiment it is possible to use transport devices such as e.g. transport stars in which the transport path at least in segments is formed substantially meandering. This embodiment furthermore allows a particularly compact construction.

Preferably it is provided that in the apparatus for sterilising containers, on the side of the transport path opposite the first external application device, a further external application device is arranged wherein the external application device and the further external application device particularly preferably are arranged offset along the transport path.

This embodiment with two external application devices opposite each other in relation to the transport path is advantageous as in this way, the containers can be exposed to charge carriers from both sides without rotation of the containers about their longitudinal axis. The transport device can therefore be substantially simplified and e.g. no mechanism is required for complete rotation of the containers about their longitudinal axis. If despite the opposing external application devices, sterilisation in the edge regions is still not sufficient, a swivel movement of the containers is conceivable. A swivel movement substantially means a rotation of the containers about fractions of a complete revolution. The control means necessary for this is substantially simpler than that for complete rotations yet nonetheless guarantees adequate sterilisation of all external surface regions of the container.

To prevent the charge carriers from being accelerated directly against each other, which e.g. could lead to particularly high charge carrier densities in the overlap region of the charge carrier clouds emitted or to damage to the external application devices from constant exposure to charge carriers which are emitted in their direction by the opposite external application device, the external application devices are preferably arranged offset along the transport path at an angle between 2 and 20°, particularly preferably between 5 and 10° of a circle of curvature of the transport path.

Therefore preferably the maxima of the charge carrier clouds emitted by the external application devices in the direction of the transport path are arranged spaced along the transport direction of the containers by at least 2 cm, preferably at least 5 cm, particularly preferably at least 10 cm and preferably maximum 200 cm, preferably maximum 100 cm, particularly preferably maximum 50 cm. As a result during transport the containers first enter the influence region of one external application device and are exposed to charge carriers from this. At a later time when the container reaches an influence region of the other external application device located downstream, it is exposed to charge carriers emitted by the latter. Thus the influence regions of the two external application devices can overlap.

Preferably at least one external application device is arranged substantially outside a clean room. The phrase "substantially outside the clean room" in this context means that a majority of the external application device is accessible from the outside without opening the clean room—and hence without possible contamination of the clean room—but the charge carrier outlet window is arranged in a wall of the clean room so that the charge carriers can be emitted by the external application device into the clean room and onto the container to be sterilised.

It is advantageous if the apparatus for sterilising containers is arranged in a region of the transport path in which the first external application device is arranged, and surrounded at least in segments by a radiation screening apparatus with at least one outer radiation screening apparatus and an inner radiation screening apparatus by which radiation emitted by the first external application device can be at least partly absorbed.

The embodiment with two radiation screening devices allows the formation of a transport channel which extends between the two radiation screening devices and in which the containers can be transported. The inner radiation screening device in this respect means a radiation screening device which screens out charge carriers in the direction of an inside of the apparatus.

Since advantageously no personnel is present in this region, this radiation screening device can where applicable be made weaker than the outer radiation screening device. This preferably also shields the environment in which personnel may—at least temporarily—be present, against the charge carriers and/or radiation. In the preferred embodiment of the arrangement of the external application devices along a segment of a circle circumference, the inner radiation screening device lies radially inside in relation to the transport path and a circle centre point, and the outer radiation screening device lies radially outside in relation to the transport path and a circle centre point.

The outer radiation screening device is consequently preferably arranged on a radially outer side of a curved transport path. As the external application devices preferably constitute the strongest charge carrier generating devices, particularly strong screening is required in their influence region. Preferably the radiation screening device arranged in this region therefore has stronger screening properties than the radiation screening device arranged along another region of the transport path.

Due to the curvature of the transport path in the region of the external application devices, it is possible for the external screening device to reflect or deflect radiation and/or charge carriers—preferably at least twice, particularly preferably several times—preferably in the direction of the containers to be sterilised.

An apparatus for sterilising containers is preferred in which the radiation screening apparatus has one portion which is stationary during transport of the containers along the transport path and another portion which is mobile in relation to the first portion during transport of the containers along the transport path.

With this embodiment it is possible for gripper or holder elements to follow the movement of the relatively mobile parts of the radiation screening apparatus and move (at least with one vector component) parallel to the transport direction of the containers.

Advantageously the speed of the relatively mobile portion of the radiation screening apparatus can be adapted—at least in a segment of the transport path—to a speed with which the containers are moved along the transport path.

Preferably the gripper or holder elements penetrate the relatively mobile portion of the radiation screening apparatus at least in segments so that a part of the gripper or holder elements is arranged inside the transport channel and can there grip or hold the containers. Another part of the gripper or holder device is preferably arranged outside the transport channel. This part lying outside can for example contain maintenance-intensive components so that their maintenance is possible without having to open the sterile transport channel. Preferably elements of a lifting, turning, swivelling and/or transport mechanism lie outside the sterile transport channel.

In particular in the treatment of preforms, it is necessary to adapt the lift mechanism to the smaller dimensions of the preforms in comparison with the finished containers.

Preferably the containers are held or transported at least in the region of external sterilisation by a substantially one-piece clamping sleeve.

An apparatus for sterilising containers is preferred in which the internal application device for sterilising at least a segment of an inner wall of containers comprises an acceleration device with a lower acceleration voltage than an acceleration device of the first external application device.

The internal application device must be introduced at least in portions into the interior of the container. Therefore special requirements apply to its dimensions, which is disadvantageous for the strong screening, large transformers, bulky cooling elements and other large components. In particular for internal sterilisation of preforms, because of their smaller extension, there is no need for particularly strongly accelerated charge carriers. Often preforms have an internal diameter of <5 cm, <3 cm or even <2 cm so that the charge carriers do not have cover great distances between a charge carrier outlet window located inside the container and the inner surface of the container. Therefore for the internal application device in this case low acceleration voltages are sufficient. A reduction in acceleration voltage to the extent necessary offers benefits in energy efficiency, operating costs and costs for adequate shielding of the environment from charge carriers and/or radiation.

In comparison the external application device emits charge carriers over a larger region so that there higher acceleration voltages and/or greater charge carrier quantities are required. Consequently in its vicinity, stronger screening is advantageous.

To be able to design the external application device nonetheless as compactly as possible and at the same time be able to apply charge carriers to the entire necessary surface region of the container, in a preferred embodiment of the apparatus for sterilising containers at least the first external application device, preferably also a further external application device, has a substantially rectangular or oval charge carrier outlet window wherein preferably at least one longitudinal axis of the charge carrier outlet window is tilted in relation to a longitudinal axis of the container to be exposed to charge carriers. Preferably the entire external application device is tilted in relation to a longitudinal axis of the container to be exposed to charge carriers. Preferably the charge carrier outlet window is substantially rectangular.

The phrase "tilted in relation to the longitudinal axis of the container to be exposed to charge carriers" means that the charge carrier outlet window or external application devices has a main axis which is tilted in relation to the longitudinal axis of the container to be exposed to charge carriers. The main axes in this respect are the axes which constitute a preferred direction or maximum extension in one direction of the outlet window or the external application device housing, or axes perpendicular thereto. Examples are the large half-axis and small half-axis of an oval (elliptical) outlet window or external application device housing, the centre vertical of a rectangular outlet window or external application device housing, or others.

Preferably the main axes of the external application devices are tilted in relation to each other.

With a tilted arrangement of the external application devices and/or charge carrier outlet window, the segment in which a container is sterilised during its transport along the transport path can be extended. At the same time however it can also be guaranteed that the container is exposed to the charge carrier over its entire height or length at least over the entire region of the outer surface to be sterilised. As shown in detail in the description for FIG. 4, because of the tilt of the charge carrier outlet window and/or external application device, a region is created in the form of a parallelogram in which the surface of the container swept during its transport and the charge carrier cloud emitted by the external application device overlap.

This region is dimensioned such that the container passes through this with all external surfaces to be sterilised. Preferably the parallelogram delimiting this region therefore has a height (above the base line) which corresponds at least to the length or height of the container. By tilting, the length of the transport path in which the respective part of the external container surface is sterilised is extended, preferably by a ratio which corresponds approximately (disregarding the scatter effect of the charge carrier) to the sine of the tilt angle to the width of the charge carrier outlet window.

Also preferred is an apparatus for sterilising containers in which the apparatus comprises an insertion device by means of which the internal application device at least in portions can be introduced into the interior of a container, wherein the container and the second charge carrier outlet device are mobile relative to each other, preferably in a longitudinal direction of the container.

In a further preferred embodiment of the apparatus for sterilising containers, a segment of a carrier plate mobile in relation to the first portion of the radiation screening apparatus at least part of the time contacts a sealing and/or sterilisation medium present in a channel, in order to seal a clean room extending at least in segments along the transport path. The carrier plate is preferably mobile in synchrony with a portion of the radiation screening apparatus mobile relative to the first portion of the radiation screening apparatus. Preferably the carrier plate forms a boundary of the clean room.

The transport channel is then closed by a hydraulic seal against the environment on the side of the relatively mobile portion of the radiation screening apparatus. Preferably this seal is a ring which rotates according to the movement of the containers along the transport path and screens the transport path or segment of the transport path in which external sterilisation takes place.

Thus it can be guaranteed that the interior of the transport channel is closed against the environment and no foreign bodies, contaminants, micro-organisms, spores or other can penetrate the transport channel. Preferably the medium is a medium which has both sealing and sterilising properties. Further preferably this is a liquid or semiliquid (low viscosity) medium so that a positive pressure can be built up in the interior of the transport channel which prevents the inflow of ambient air and the contaminants it carries into the sterile transport channel. However gasses are also possible as a medium, wherein these preferably are set or held in flow so as to prevent the penetration of external substances into the clean room. In particular accordingly a flow is maintained which runs from the direction of the clean room in the direction of the environment.

Preferably below the channel in which the sealing or sterilisation medium is present, a further channel is arranged into which medium can be introduced e.g. drawn in from the upper channel. The sealing and/or sterilisation medium is preferably a watery solution of a sterilising active substance (sterilisation agent). Particularly preferably as a sealing agent a gas flow is used, preferably an air flow, in particular (filtered) ambient air which by its flow prevents the penetration of contaminants into the interior of the clean room.

Preferably furthermore an apparatus for sterilising containers is provided in which the segment of the carrier plate which is mobile in relation to the first portion of the radiation screening apparatus can be separated at least part of the time from the sealing and/or sterilisation medium present in the channel, in order to allow access to the clean room extending along the transport path, in particular for maintenance and/or cleaning. In particular it is provided that the portion of the radiation screening apparatus mobile relative to the first portion, in particular an upper part of the external sterilisation device, can be removed upwards. As a result there is a possibility of opening the transport channel, previously closed against the environment, in order to clean this. For example in this way very easily an additional disinfectant or sterilisation agent can be introduced into the transport channel. Also it is possible to remove any containers in the transport channel which have become detached from the holding devices, in order to prevent damage or loss of further containers.

Furthermore, an embodiment of the apparatus for sterilising containers is preferred in which the apparatus has a lift device by means of which the containers can be moved along their longitudinal direction during their transport along the transport path. Preferably such a lift device is located in the region of a transport device which transports the containers during their external sterilisation. As a result it is possible to orient the containers in relation to the external application device, in particular during external sterilisation. In particular it is possible as a result, with charge carrier outlet windows tilted in relation to the container longitudinal axis, to position the containers such that the proposed region of the external container surface is exposed to charge carriers.

Preferably this lift mechanism has a motor and a threaded rod guide which are adapted to the small space available in the region of the external sterilisation device. Said movement of the containers in their longitudinal direction could however also be achieved by the use of guide rails or control curves.

The charge carriers are in particular electrons, it would also however be conceivable to use other charge carriers such as ions.

The charge carrier outlet window is particularly preferably made of a material selected from a group of materials containing titanium, quartz glass, diamond, combinations thereof and similar.

Furthermore, a plant for treating containers is the object of the present invention which comprises at least one apparatus of the type described above, wherein this apparatus is arranged preferably downstream of a heating device for heating plastic preforms and upstream of a filling device, preferably upstream of a forming device for containers.

With such a plant it is possible to carry out an internal and external sterilisation of containers in particular in the high cycle rates and throughput counts used in production and filling of containers.

In particular if the described apparatus is arranged downstream of a heating device and upstream of a forming device, rapid sterilisation and rapid transport through the apparatus are required. If the sterilisation process or transport through the sterilisation apparatus takes too long, there is a risk of cooling of the containers, in this case the preforms. Preferably the apparatus is therefore suitable for transporting the containers along the transport path and sterilising them within a time window of less than 20 seconds, preferably less than 15 seconds, particularly preferably around 11 seconds.

Preferably the plant comprises a transport device which moves the containers along a predefined transport path, in particular during their sterilisation. Advantageously the transport device is a rotatable carrier on which is arranged particularly preferably a plurality of gripper elements.

Preferably the plant comprises a device for filling containers and the apparatus according to the invention is arranged upstream of this device.

It is further preferred if the plant has at least one transport element, preferably a transport star, which is suitable for taking a container from an apparatus for sterilising containers and delivering them to a device for forming containers.

Preferably such a plant has a so-called lock star for insertion and discharge of containers into and out of an apparatus of the type described above. Preferably these two lock stars are separate. In particular because of the pitch spacing modified within the apparatus, an identical design of the lock stars is not possible.

A further essential aspect of the invention is a method for sterilising at least a segment of an inner wall and a segment of an outer wall of containers by means of accelerated charge carriers, wherein the container is exposed to the charge carriers from at least one first external application device for sterilising at least a segment of an outer wall of containers and an internal application device for sterilising at least a segment of an inner wall of containers, wherein the internal application device at least in portions is introduced through an opening into the container in order to apply the emitted charge carriers to an inner wall of the container, wherein the containers are transported along a transport path by means of a transport device during their sterilisation, wherein along a segment of the transport path of the containers between the first external application device and the internal application device is arranged a pitch change device which changes the distance between two containers succeeding each other along the transport path.

With this method it is therefore possible to sterilise containers both on the outside and on the inside at least in segments in high cycle rates. The pitch change device arranged between the external application device and the internal application device allows adjustment of the distance necessary for the sterilisation process at both the external application device and the internal application device, and hence adjustment also of the transport speed of the containers.

A variant of the method for sterilising containers is preferred in which the preforms, in particular preforms for drinks containers and/or other fluid media, are sterilised. This has the advantage that in comparison with the finished moulded containers, substantially smaller surface areas need be sterilised and the process can therefore be structured more efficiently. Also the entire apparatus can be dimensioned smaller, which results in a significant weight reduction. Furthermore, as a result a higher process stability is possible of the charge carrier application devices i.e. the external application device and internal application device, as the energy used and the resulting window loading are smaller because of the dimensions of a preform.

Further preferred is a variant of the method for sterilising containers in which the container is transported along a transport path which is curved at least in one segment in which is arranged the external application device for sterilising at least a segment of an outer wall of containers.

Also a variant of the method for sterilising containers is preferred in which, on the side of the transport path opposite the first external application device, a further external application device is arranged, wherein the first external application device and the external application device are preferably arranged offset along the transport path. Preferably the two external application devices are offset to each other by an angle between 2 and 20°, particularly preferably between 5 and 10°, of a circle of curvature of the transport path.

BRIEF DESCRIPTION OF THE DRAWINGS

Further advantages and embodiments arise from the enclosed drawings.

These show.

DETAILED DESCRIPTION OF THE INVENTION

Figure 1:
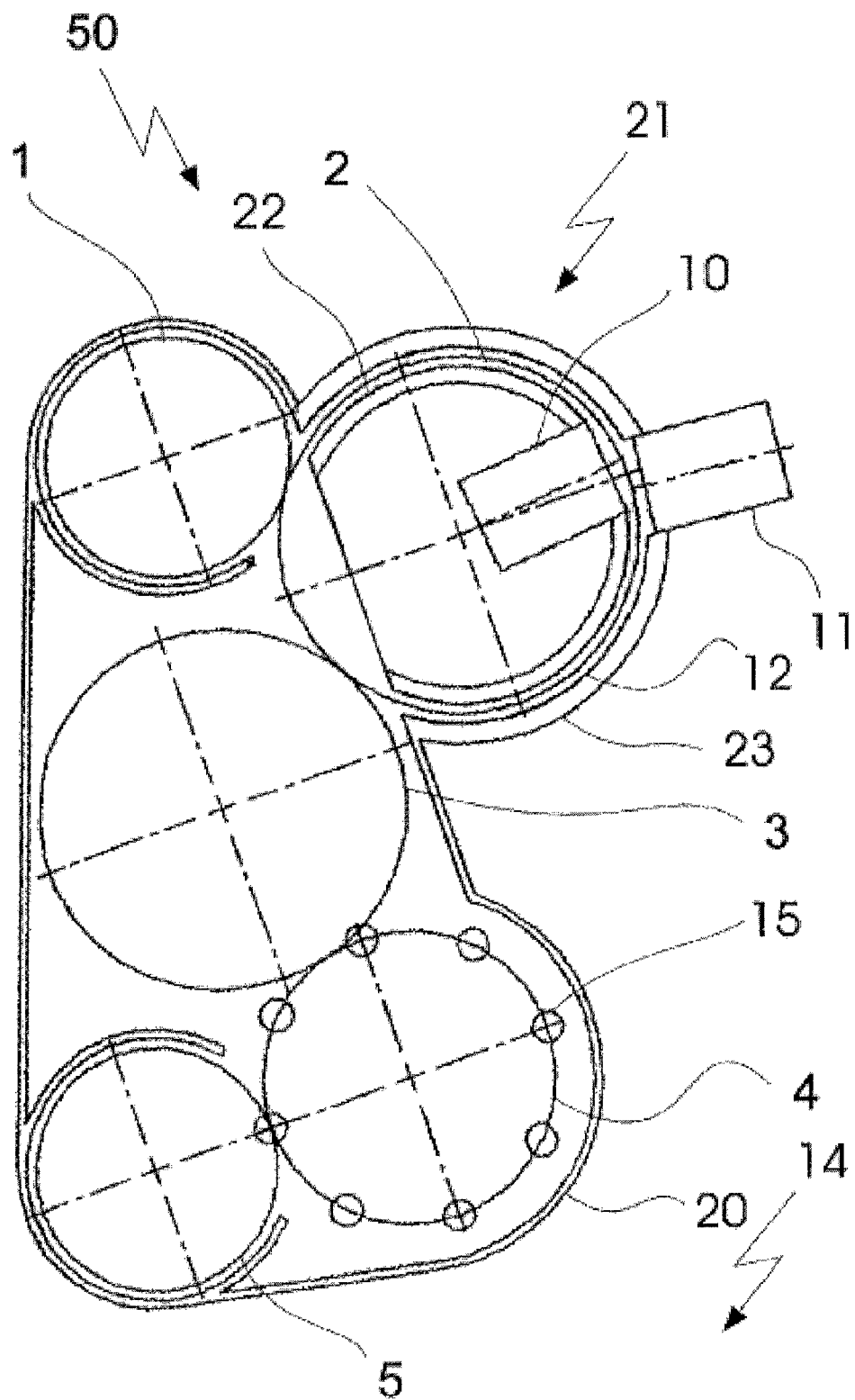
FIG. 1 a diagrammatic depiction of a top view of an apparatus for sterilising containers.

FIG. 1 shows a diagrammatic depiction of a top view of an apparatus 50 for sterilising containers 19. This has a transport device 1 for receiving containers 19 which in the embodiment shown is designed as an inlet star 1. Downstream of the inlet star 1 is a treatment zone for the containers 19 in which external sterilisation takes place. To be able to expose the containers 19 to charge carriers, the containers are delivered to a transport device 2 which transports the containers past the external application devices 10 and 11. During transport the containers 19 are exposed to charge carriers which are emitted by the external application devices 10 and 11. To allow full sterilisation all round, two external application devices 10 and 11 are provided, wherein the first external application device 10 is arranged on the radially inner side of the transport path and a second external application device 11 is arranged on the radially outer side of the transport path. However it would also be conceivable to omit one of the two external application devices and instead achieve complete sterilisation of the container by (e.g. complete) rotation of the container.

To shield the environment 14 from the radiation emitted by the external application devices 10 and 11, in particular from the external application device 10 emitting radiation towards the outside, this region is surrounded by a strong radiation screening apparatus 21. The radiation screening apparatus here consists of several radiation screening devices 22 and 23 together which shield the transport channel in different directions. In the view shown, one outer radiation screening device 23 and one inner radiation screening device 22 are depicted. Screening in the upward and downward direction is not shown.

By the curvature of the transport path and hence also of the radiation screening apparatus 21 in the region of the external application devices 10 and 11, it is possible for radiation to be reflected between the outer radiation screening device 23 and the inner radiation screening device 22, and hence the region in which sterilisation takes place is larger than merely the region directly in front of the external application devices 10 and 11 or their charge carrier outlet windows.

To allow the containers to remain for as long as possible in the region in which sterilisation of their outer surface takes place, a low transport speed and short distance between the containers is advantageous. Due to the short distance between two adjacent containers along the transport path, a high throughput can be achieved even at low transport speed. Furthermore with a small pitch interval, it is advantageous that few charge carriers (or radiation) can pass unused for the sterilisation process between the containers.

In order however to restore a larger pitch interval, i.e. a greater distance between two containers directly succeeding each other along the transport path as required for devices needed downstream, immediately after the external sterilisation device downstream is a pitch change device 3 to change the distance between two containers succeeding each other along the transport path. By means of this pitch change device 3, in this case a pitch change star, it is possible to vary the spacing of containers such that handover is possible to an internal sterilisation device 15 arranged downstream.

The internal sterilisation device has a plurality of internal application devices 15 which can be introduced at least in portions into the containers. These are arranged along or around a transport device 4 which transports the containers along the transport path during treatment of an inner surface of the containers. For internal sterilisation, each of the internal application devices 15 has a so-called radiation finger which is dimensioned such that it fits through the opening of the container. The other part of each internal application device 15 is normally however substantially larger than the radiation finger and in particular has a greater diameter. The diameter is normally also greater than that of each individual container to be sterilised, so that the distance between two containers directly succeeding each other along the transport path in the region of the internal sterilisation device is determined no longer by the diameter of the containers but by a minimum spacing between two adjacent internal application devices 15. In particular for internal sterilisation of preforms, it is therefore necessary to enlarge the distance between two containers directly succeeding each other along the transport path and adapt this to the distance between two adjacent internal application devices 15.

From the internal sterilisation device, after treatment with an internal sterilisation device 15 the containers are delivered to a downstream transport device 5. This transport device 5, like the transport device 1, is designed as a transport star 5. Transport stars 1 and 5 however differ in their construction. At least the pitch spacing with which they transport containers differs. The transport star 5 takes the containers, sterilised on the inner surface, from a transport device 4 which transports the containers during internal sterilisation, and delivers them to a further transport device (not shown) or to a container treatment device. For example, a container treatment device arranged downstream of the transport star 5 could be a forming device or a filling device. The individual internal application devices 15 advantageously apply charge carriers to the entire inner surface of the containers 19.

Figure 2:
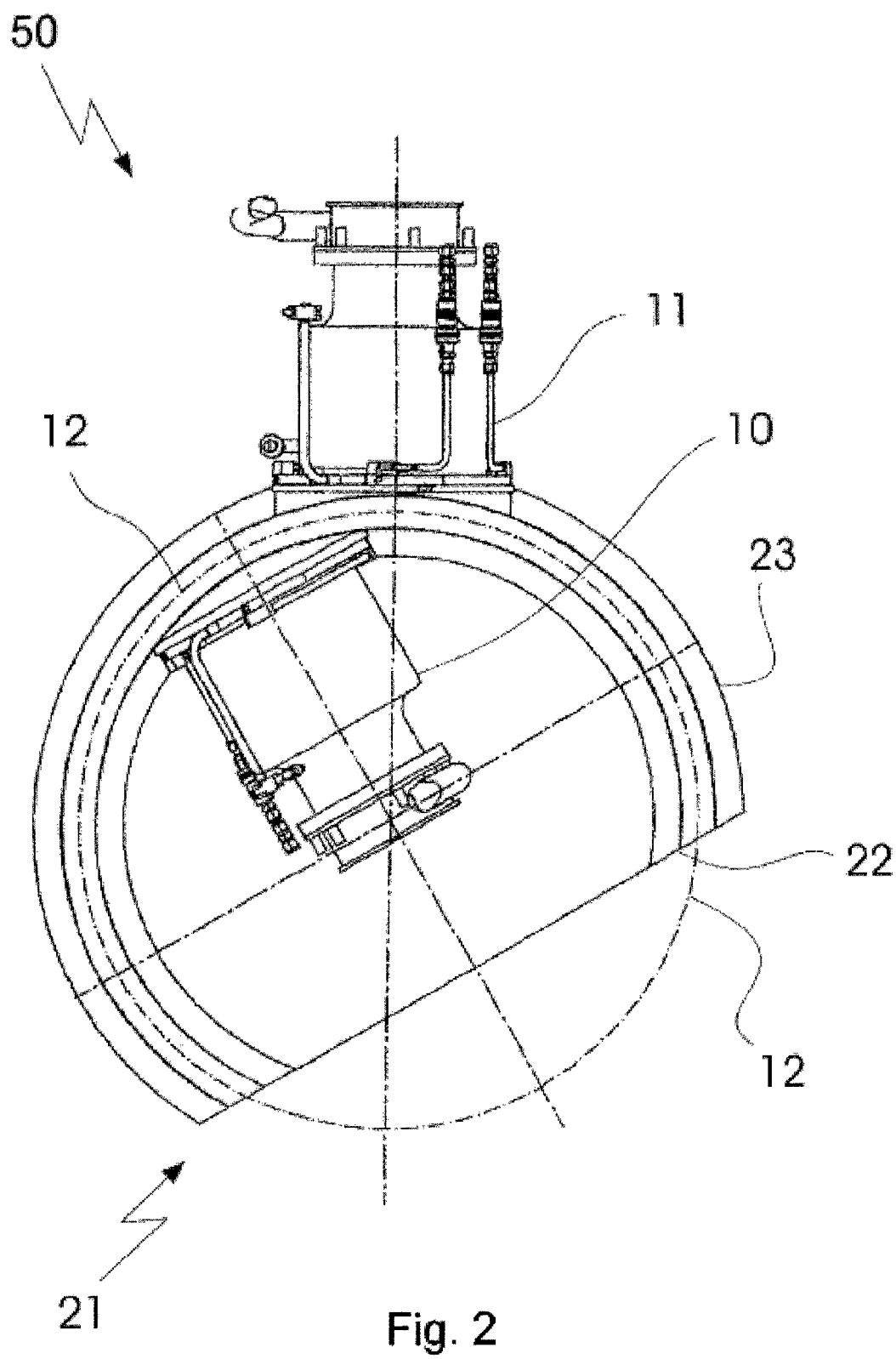
FIG. 2 a diagrammatic depiction of a top view of a region of an apparatus for sterilising containers in which the external sterilisation of the containers takes place.

FIG. 2 shows a diagrammatic depiction of a top view of a region of a device 50 for sterilising containers 19 in which the external sterilisation of the containers 19 takes place.

In particular FIG. 2 shows a segment of the transport path along which the external sterilisation of the containers 19 takes place. For external sterilisation the containers pass by the external application devices 10 and 11. These external application devices 10 and 11 are arranged on different sides of the transport path and are therefore suitable for applying charge carriers to a container 19 from different sides. Thus the transport mechanism for the containers 19 can be simplified since a complete revolution of the containers 19 is not necessary for full application of the charge carriers all round. Advantageously the external application devices 10 and 11 apply charge carriers to the entire outer circumferential surface of the containers 19.

The two external application devices 10 and 11 are not directly opposite each other but arranged offset to each other along the transport path of the containers 19. On transport of the containers along the transport path which runs clockwise (to the right) in the view shown in FIG. 2, the containers first reach the influence region of the external application device 10 lying radially on the inside and accelerating charge carriers radially towards the outside. There an external surface lying radially on the inside in relation to the transport device 2 of the container is exposed to charge carriers.

Only slightly further downstream do the containers 19 enter the influence region of the external application device 11 lying radially on the outside and accelerating charge carriers radially towards the inside. The outer surface of the container, lying radially on the outside in relation to the transport device (2) and lying in the charge carrier shadow of the container during treatment by the other external application device 10, is exposed in this region to charge carriers from the external application device 11.

The two external application devices 10 and 11 are offset to each other by a predefined angle in relation to the centre or rotation axis of the transport device 2. This offset guarantees that the charge carriers of the two external application devices 10 and 11 are not accelerated directly onto each other, whereby in long-term operation damage could be caused to the external application devices 10 and 11. Also the containers 19 can become heated when exposed to charge carriers as they at least partly absorb the kinetic energy of the accelerated charge carriers and convert this into thermal energy. By the offset arrangement of the external application devices 10 and 11 therefore overheating and hence possible damage of the containers can be avoided with simultaneous charge carrier application from two external application devices 10 and 11.

In addition the length of the segment of transport path in which the containers are exposed to charge carriers is extended. With a cloud-like propagation of charge carriers in which the charge carriers are also subjected to diffusion, in addition to the preference direction predefined by the charge carrier acceleration device, an overlap of the emitted charge carrier clouds is thus possible so that the containers 19 remain longer in the common charge carrier cloud of both external application devices 10 and 11.

To shield the environment 14 from the emitted charge carriers and/or from the radiation emitted on charge carrier generation, the region of the external sterilisation is surrounded with strong radiation screening apparatus 21. This consists at least of radiation screening devices 22 and 23 which surround the transport path on different sides. With regard to the centre of the transport device 2 (in particular the rotation axis of the transport device 2), one radiation screening device 23 is arranged radially outside the transport channel and one radiation screening device 22 is arranged radially inside the transport channel. The screening of the transport channel vertical to the drawing plane is not shown.

The radiation screening apparatus 21 in the region of the external application devices 10 and 11 follows the curvature of the transport path and thus allows radiation to be reflected between the outer radiation screening device 23 and the inner radiation screening device 22. In this way the region in which the containers are exposed to charge carriers and/or energy-rich (sterilising) radiation can be enlarged.

Figure 3:
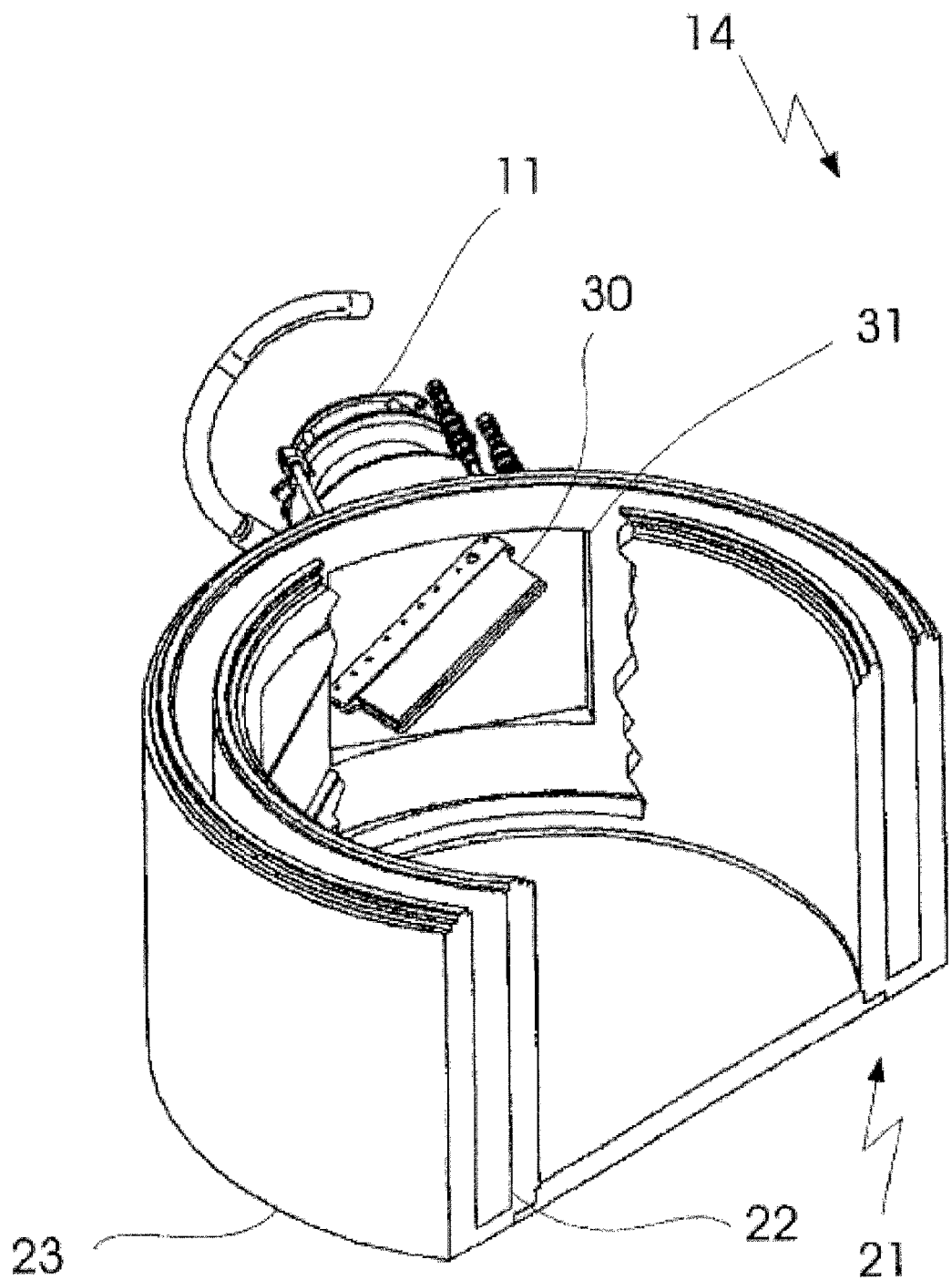
FIG. 3 a diagrammatic depiction of an oblique view of a region of an apparatus for sterilising containers in which the external sterilisation of containers takes place, additionally depicting a charge carrier outlet window.

FIG. 3 shows a diagrammatic depiction of a oblique view of a region of an apparatus for sterilising containers in which the external sterilisation of the containers 19 takes place, with the additional depiction of a charge carrier outlet window 30.

As in FIG. 2, the transport channel surrounded by the radiation screening apparatus 21, and an external application device 11 are shown. The external application device 10 lying radially inside in relation to the centre of the transport device 2 (not shown) and the part of the inner radiation screening device 22 lying in this region are not shown in order to be able to depict the arrangement of the external application device 11 and its charge carrier outlet window 30.

As evident in FIG. 3, the external radiation screening device 23 is interrupted in the region of the external application device 11 to allow entry into the transport channel of the charge carriers generated in the external application device 11. For this a housing of the external application device 11 terminates the transport channel flush, in order to prevent contamination of the transport channel designed as a clean room. The flush connection of the external application device 11 is achieved by a fixing element 31, in this case a fixing flange. To allow unhindered passage of the charge carriers into the clean room or transport channel, the external application device 11 has a charge carrier outlet window 30 through which charge carriers can be accelerated by a charge carrier generation device in the direction of the transport channel. Thus, it is possible for the charge carriers to reach the interior of the clean room through the charge carrier outlet window 30 and there meet a container 19 transported along the transport path.

The charge carrier outlet window 30 has a substantially rectangular cross section. Although other geometries of the charge carrier outlet window 30 are also possible such as circles, ovals and/or squares as a special form of a rectangle, a rectangular form or a parallelogram form with uneven sides is preferred. In the rectangular form shown, the main axes are oriented tilted in relation to the transport path (and its horizontal vector part). Thus, it is possible for a container 19 passing by a charge carrier outlet window 30 to remain longer in the influence region of the charge carrier cloud. Thus with comparable sterilisation power, a more compact construction can be achieved.

In particular if due to a lift mechanism the container 19 can be raised during transport along the orbit of the transport channel and can thus follow the course of the charge carrier outlet window 30, an extension of the treatment region is possible.

Figure 4:
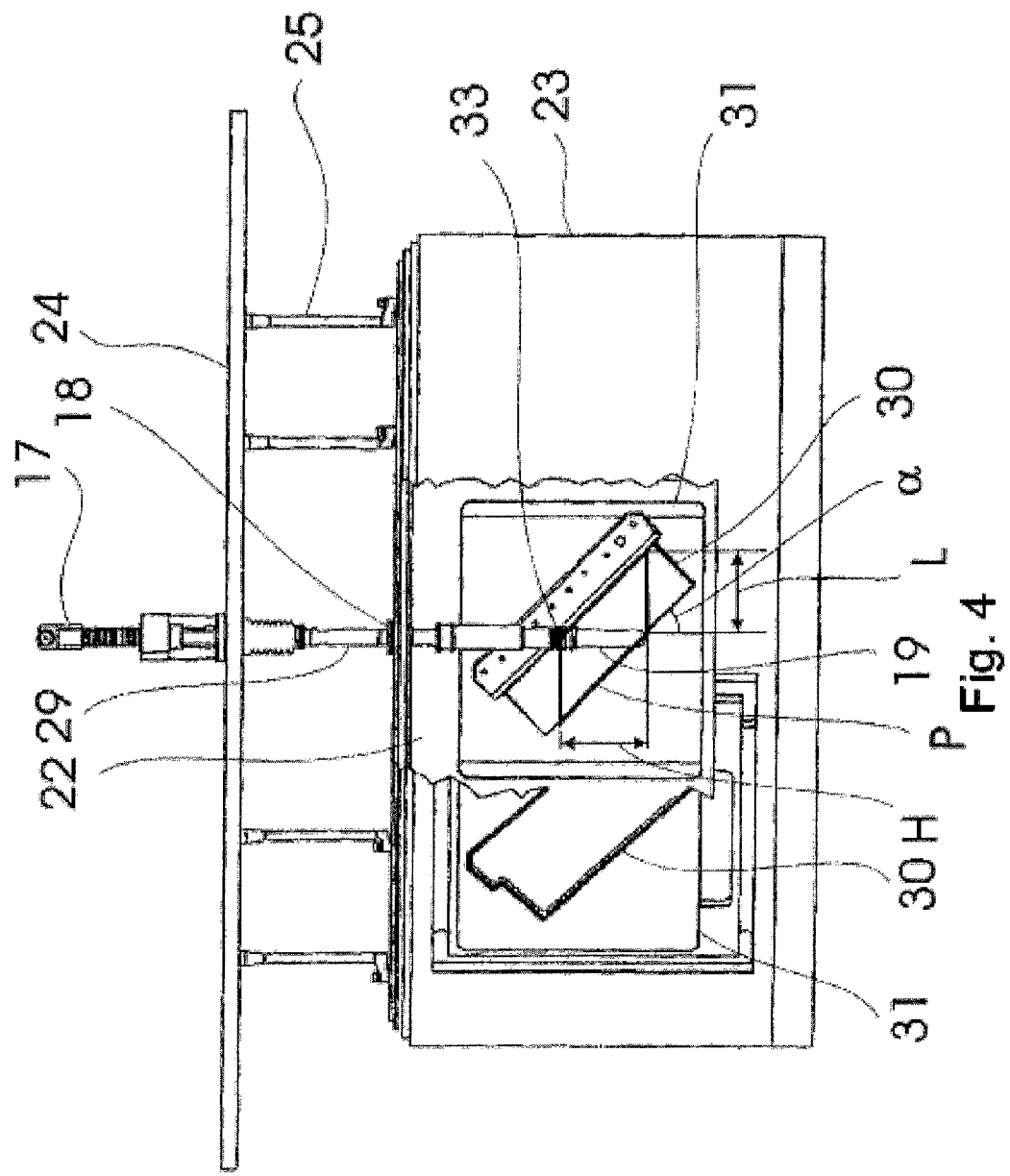
FIG. 4 a diagrammatic depiction of a side view of a region of an apparatus for sterilising containers in which external sterilisation of containers takes place, additionally depicting the charge carrier outlet window.

This is evident in particular in the diagrammatic depiction of a side view shown in FIG. 4. FIG. 4 shows a side view of a region of an apparatus 50 for sterilising containers 19 in which the external sterilisation of containers takes place, with the additional depiction of the charge carrier outlet window 30. To show that the charge carrier outlet windows 30 of several external application devices 10 and 11 can be arranged tilted by an angle $\alpha$ in relation to the transport path (or its horizontal vector part) and/or the container longitudinal axis, several charge carrier outlet windows 30 are shown. These can also be arranged tilted in relation to each other. Thus, it is possible that the containers 19 which are raised in the region of an external application device 10 along the transport path (or moved in the direction along the container longitudinal axis) can be lowered again in the region of the next external application device 11 along the transport path (or moved in the opposite direction in relation to the first movement along the container longitudinal axis).

By the orientation of the charge carrier outlet window 30 tilted by an angle $\alpha$ in relation to the container longitudinal axis, the section along which direct external sterilisation can take place on transport of the container 19 is extended. Even on an exclusive movement of the container 19 perpendicular to its longitudinal axis, the section of transport path along which a segment of the outer wall of the containers 19 is exposed to charge carrier radiation is extended. If we take for example the side sheathing of the base of a container 19, this is in the direct influence of the charge carriers emitted vertically by the external application device 11 onto the container along a segment of the transport path (length L of the parallelogram P drawn). This length L (according to the trigonometric functions or angular functions) is extended in relation to the width of the outlet window by a factor which corresponds to the reciprocal value of the sine of the tilt angle (i.e. the cosec of the tilt angle).

The tilt of the charge carrier outlet window 30 is here selected such that the overlap region of the charge carrier outlet window 30 with the area swept during transport of the container 19 by its vertical projection onto the charge carrier outlet window 30 has at least a height H with corresponds to the length of the container in its longitudinal direction. In the example shown the overlap region has the shape of a parallelogram of length L and height H (over L). Depending on the shape of the charge carrier outlet window 30, the orientation of the container 19 in relation to the transport path and the course of the transport path, however other geometries of the overlap region are also possible.

To allow a particularly compact design of the apparatus, as shown in FIG. 4 it is proposed that the container 19 during its transport along the transport path can also be moved along the container longitudinal axis (at least with one vector component). If the container 19 shown in FIG. 4 is moved during its sterilisation not only horizontally (or parallel to length L) but also in the height direction H, it is possible to keep the containers even longer in the influence region of the charge carriers.

For this the transport device 2 has a lift device 17. This lift device 17 is connected with a substantially horizontal carrier plate 24 which is connected with the transport device and follows its horizontal movement, in this case the rotation movement of the transport device 2. The lift device 17 is arranged outside the clean room. Thus maintenance work is simplified. A holding element 33 which carries the container during its transport along the transport path is located inside the clean room and is connected with the lift device 17. The connection between holder element 33 and lift device 17 is achieved by a carrier 29 which penetrates an upper radiation screening device 24. The upper radiation screening device 16 is mounted mobile in relation to the radiation screening devices 22 and 23 and moves parallel to the carrier plate 24. The radiation screening device 16 therefore has openings through which the carrier 29 can be introduced. To be able to maintain the screening properties of the radiation screening device 16 even on movement of the carrier 29 or the container in its longitudinal direction, the carrier 29 comprises at least in segments a screening material by means of which the openings in the radiation screening device 16 can be sealed both in relation to charge carriers and radiation, and in relation to contamination of the clean room.

To guarantee that the lift devices 17 connected with the carrier plate 24 and the openings in the radiation screening device 16 move synchronised to each other such that a lift device 17 is arranged above an opening in the radiation screening device 16, the carrier plate 24 and the radiation screening device 16 are connected together via carrier elements 25.

Figure 5:
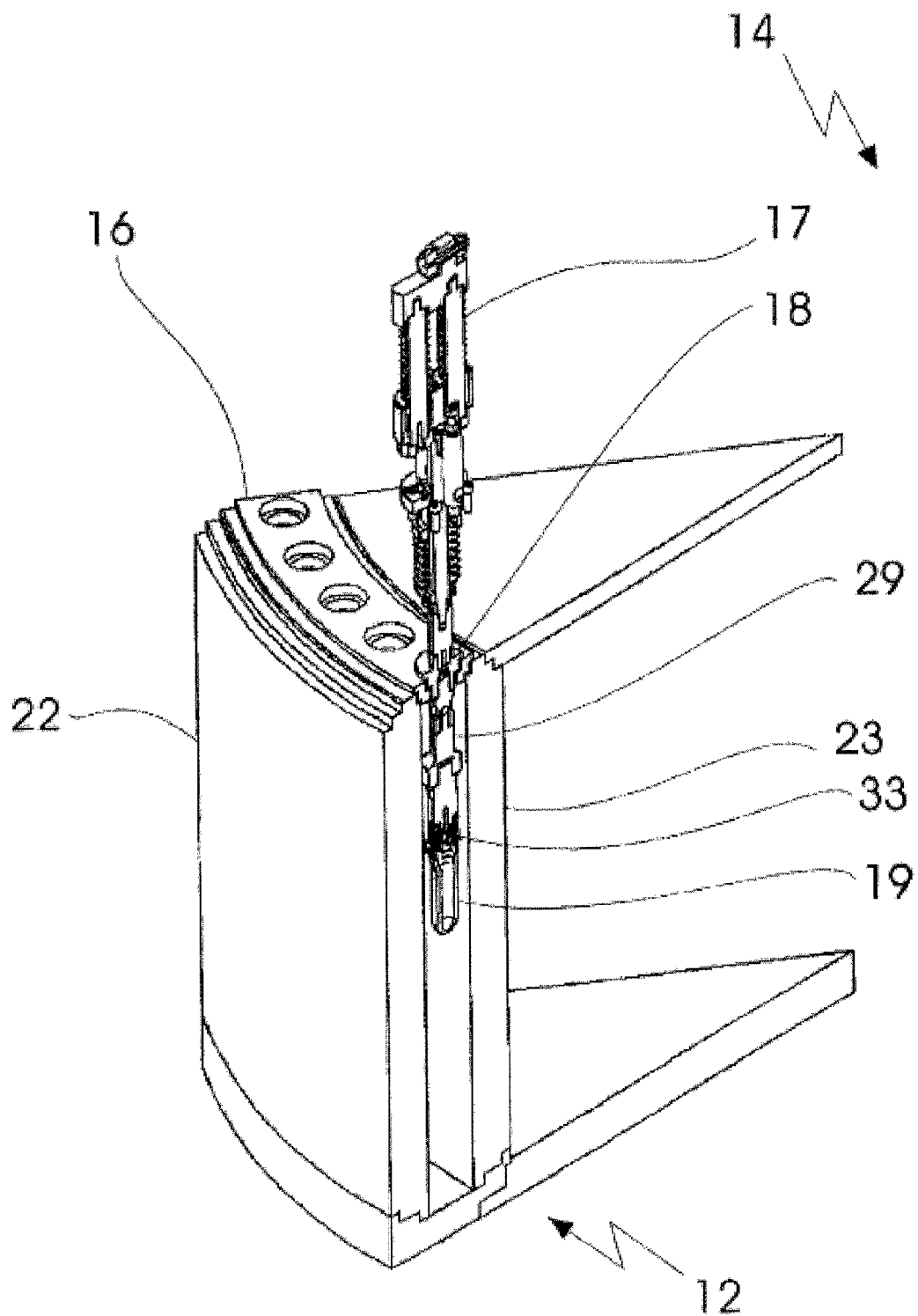
FIG. 5 a diagrammatic depiction of an oblique view of a region of a transport channel with radiation screening device.

In FIG. 5, the diagrammatic depiction of an oblique view of a region of the transport channel with radiation screening device shows how the lift movement and sealing of the clean room take place during the lift movement. The outer radiation screening device 22 and the inner radiation screening device 23 are shown between which the clean room is situated. In the example shown, the two radiation screening devices 22 and 23 are connected together at the bottom so that together in cross section they form a U-shape. Thus the underside of the clean room is also sealed against the environment 14. Both the ingress of contaminants and the emergence of charge carriers and/or radiation are prevented. The external application devices 10 and 11 are not shown for greater clarity.

Since the large external application devices 10 and 11 fitted with various supply connections are arranged stationary as far as possible, the radiation screening devices 22 and 23 are also arranged largely immobile in relation to the environment 14. In contrast an upper radiation screening device 16 is arranged mobile in relation to the radiation screening devices 22 and 23. It moves along an orbit. To avoid contamination of the clean room, between the radiation screening devices 22 and 23 and the radiation screening device 16 a seal is provided, preferably a hydraulic seal or a "water lock". The sealing material here is a fluid e.g. preferably a watery solution of a sterilisation agent. The radiation screening device 16 has openings through which the carriers 29 can penetrate. On the clean room side these carriers 29 have a holding element 33 which grips the container 19. Preferably this is a mandrel which engages in the mouth of the container. Outside the clean room 12 the carrier 29 is connected with a lift device 17 which allows movement of the carrier 29 and hence also the container in the longitudinal direction ($L_1$).

To prevent the escape of charge carriers and/or radiation from the clean room interior into the environment, the carrier 29 has a separate radiation screening device 18 which can close the openings on the environment side and/or on the clean room side. Preferably the carrier 29, in the segment which penetrates the opening in the radiation screening device 16 during a lift movement, has an external diameter which is only slightly smaller than the internal diameter of the opening. Preferably this region is secured by at least one seal largely impermeable to charge carriers and/or radiation, against the escape of charge carriers and/or radiation to the environment. To prevent the introduction of contamination from the environment into the interior of the clean room, preferably on the clean room side a seal is provided by means of a sealing element (not shown) e.g. a gaiter 34.

In general it is therefore proposed that at least one radiation screening device 16, 22, 23 also forms at least partly the clean room boundary.

Figure 6:
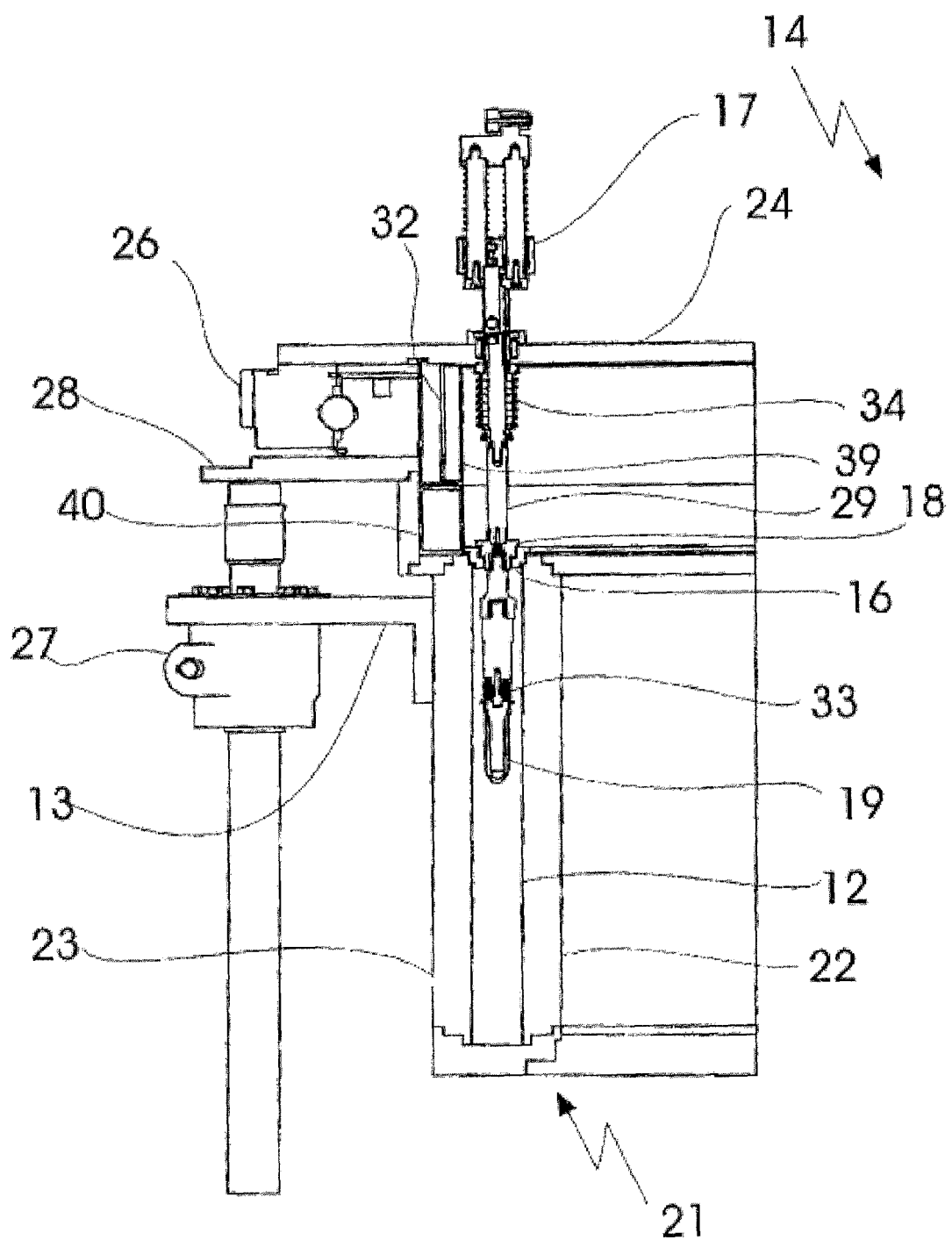
FIG. 6 a diagrammatic depiction of a side view of a region of the transport channel in closed state.

FIG. 6 shows a diagrammatic depiction of a side view of a region of the transport channel 12 in closed state. The screening (against radiation and/or charge carriers) and the seal (against contamination of the clean room) are particularly clearly evident in this figure.

In the example shown, as in FIG. 5, the clean room 12 with its surrounding radiation screening apparatus 21 with radiation screening devices 22 and 23 is shown. In the interior of the clean room 12 is a container 19 which is carried by a holding element 33. The holding element 33 is connected with a carrier 29 which penetrates an opening in the radiation screening device 16. By thickening of the carrier 29 (radiation screening device 18), a secure seal of the openings is achieved and emergence of charge carriers and/or radiation avoided. Since in the example shown, the clean room extends above the radiation screening device 16, a seal to prevent contamination is not necessary in the region of the openings of the radiation screening device 16. In relation to the stationary radiation screening devices 22 and 23, the clean room is however sealed by a hydraulic seal in the transition region to the radiation screening device 16 mobile relative thereto. At the top the clean room 12 is delimited by the carrier plate 24 on which is arranged the lift device 17. The carrier 29 also penetrates the carrier plate 24. In this transition region at least part of the carrier which can be arranged both inside or outside the clean room is sealed by means of a gaiter 34. Thus the introduction of contamination can be avoided when the carrier re-enters the clean room 12.

Reference numeral 32 designates a boundary element which constitutes a boundary between the sterile and the non-sterile region of the device 50. This boundary element 32 is immersed in a fluid which is guided in the fluid channel 39. Preferably the fluid is a watery sterilisation agent, but other fluids or gasses are possible. In particular an embodiment is provided in which the seal of the clean room 12 is achieved by a special air guide in the region of the radiation screening devices 16, 22 and 23 mobile relative to each other. For this the additional channel 40 is provided through which air is extracted continuously. Due to the slight positive pressure maintained in the interior of the clean room 12, a continuous gas flow from the clean room 12 can be maintained, which prevents the inflow of contaminants.

To open the clean room 12, a further lift mechanism 27 is provided which raises the carrier plate 24 including all lift devices 17, carriers 29, holding elements 33 and containers 19 arranged thereon and the upper radiation screening device 16. For this the lift mechanism 27 has a further carrier plate 28 with which the carrier plate 24 is connected via a ball turning connector 26. Thus, the lift mechanism 27 can be arranged stationary and need not follow the (rotary) movement of the carrier plate 24 and the transport device 2. The lift mechanism 27 can therefore be connected with the radiation screening device 23 via a connecting element 13.

Figure 7:
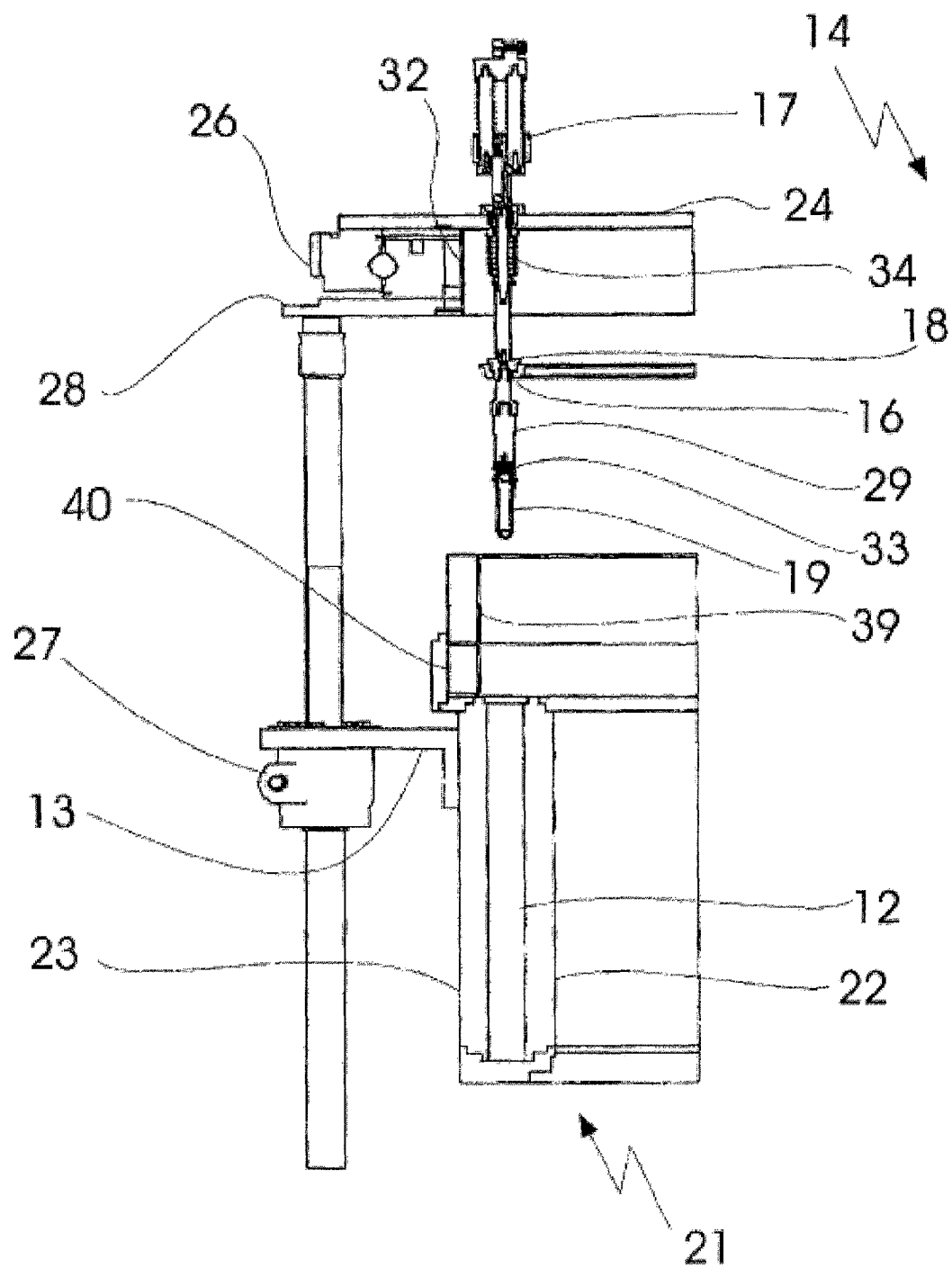
FIG. 7 a diagrammatic depiction of a side view of a region of the transport channel in opened state.

The side view shown diagrammatically in FIG. 7 shows a region of the transport channel in open state. By means of the lift mechanism 27, now extended, the carrier plate 24 including the lift devices 17, carriers 29, holding elements 33 and containers 19 arranged thereon and the upper radiation screening device 16 can be raised from the radiation screening device 21. At the same time the boundary element 32 is raised from the channel 39 so that the clean room is no longer separated from the environment 14. By raising the radiation screening device 16, also the shielding of the environment against charge carriers and/or radiation is no longer guaranteed.

By raising large parts of the transport device 2 by means of the lift mechanism 27 it is very easily possible to gain access to the interior of the clean room 12. This may for example be necessary if contaminants have collected in the clean room. This can for example be contamination or containers 19 which have become detached from the holding element 33 during transport. By sealing the raisable parts against the stationary parts of the transport device by means of a hydraulic seal, it is very easily possible to close the clean room again. After lowering the raisable parts by means of the lift mechanism 27, after immersion of the boundary element 32 in the fluid guided in the channel 39, the sterile seal of the clean room from the environment is restored.

The applicant reserves the right to claim all features disclosed in the application documents as essential to the invention where novel individually or in combination in relation to the prior art.

LIST OF REFERENCE NUMERALS

1 Transport device, inlet star
2 Transport device, external sterilisation
3 Pitch change device
4 Transport device, internal sterilisation
5 Transport device, outlet star
10 External application devices
11 External application devices
12 Clean room
13 Connecting element
14 Environment
15 Internal application devices
16 Upper radiation screening device
17 Lift device
18 Radiation screening device of the carrier
19 Container
20 Radiation screening device internal sterilisation
21 Radiation screening apparatus
22 Radially inner radiation screening device
23 Radially outer radiation screening device
24 First carrier plate
25 Carrier element
26 Ball turning connector
27 Lift mechanism
28 Second carrier plate
29 Carrier
30 Charge carrier outlet window
31 Fixing element
32 Boundary element
33 Holding element
34 Gaiter
39 First channel
40 Second channel
50 Device for sterilising
T Transport direction
H Height
L Length
α Angle
P Parallelogram

The invention claimed is:

1. An apparatus for sterilising at least a segment of an inner wall and a segment of an outer wall of containers by accelerated charge carriers, with at least one first external application device for sterilising at least a segment of an outer wall of containers and an internal application device for sterilising at least a segment of an inner wall of containers, wherein the internal application device at least in portions can be introduced through an opening into the container in order to apply the emitted charge carriers to an inner wall of the container, and a transport device for transporting the containers along a transport path during their sterilisation, wherein along a segment of the transport path of the containers between the first external application device and the internal application device is arranged a pitch change device for changing a distance between two containers succeeding each other along the transport path, wherein in a region in which sterilisation of the outer wall takes place, a distance between two containers succeeding each other along the transport path is shorter than in a region in which sterilisation of the inner wall takes place.

2. The apparatus according to claim 1, wherein the containers to be sterilised are preforms, in particular for containers for drinks and/or fluid media.

3. The apparatus according to claim 1, wherein the transport path is curved at least in a segment in which is arranged the first external application device or sterilising at least a segment of an outer wall of containers.

4. The apparatus according to claim 1, wherein on the side of the transport path opposite the first external application device is arranged a further external application device, wherein the external application device and the further external application device are arranged preferably offset along the transport path.

5. The apparatus according to claim 4, wherein the radiation screening apparatus comprises a portion stationary during transport of the containers along the transport path and another portion mobile in relation to the first portion during transport of containers along the transport path.

6. The apparatus according to claim 1, wherein a region of the transport path in which the first external application device is arranged is surrounded at least in segments by a radiation screening apparatus with at least an outer radiation screening device and an inner radiation screening device arranged to at least partially absorb radiation emitted by the first external application device.

7. The apparatus according to claim 1, wherein the internal application device for sterilising at least a segment of an inner wall of containers comprises an acceleration device with a lower acceleration voltage than an acceleration device of the first external application device.

8. The apparatus according to claim 1, wherein at least the first external application device, preferably also a further external application device, each comprises a substantially rectangular or oval charge carrier outlet window, wherein preferably at least one longitudinal axis of the charge carrier outlet window is tilted in relation to a longitudinal axis of the container to be exposed to the charge carriers.

9. The apparatus according to claim 1, wherein a segment of a carrier plate mobile in relation to the first portion of the radiation screening device at least for part of the time is in contact with a sealing and/or sterilisation medium present in a channel, in order to seal a clean room extending at least in segments along the transport path.

10. The apparatus according to at least claim 1, wherein the segment of the carrier plate mobile in relation to the first portion of the radiation screening device can for at least part of the time be separated from the sealing and/or sterilisation medium present in the channel, in order to allow access to the clean room extending along the transport path, in particular for maintenance and/or cleaning.

11. The apparatus according to claim 1, wherein the apparatus has a lift device for moving the containers along their longitudinal direction during their transport along the transport path and during their external sterilisation.

12. A plant for treating containers, wherein the plant comprises at least one apparatus for sterilising containers according to claim 1, which apparatus is arranged downstream of a heating device for heating plastic preforms and upstream of a filling device, preferably upstream of a forming device for containers.

13. A method for sterilising at least a segment of an inner wall and a segment of an outer wall of containers by accelerated charge carriers using the apparatus of claim 1, wherein the container is exposed to charge carriers from at least one first external application device for sterilising at least a segment of an outer wall of the containers and an internal application device for sterilising at least a segment of an inner wall of containers, wherein the internal application device at least in portions is introduced through an opening into the container in order to apply emitted charge carriers to an inner wall of the container, wherein the containers during their sterilisation are transported along a transport path by a transport device, wherein along a segment of the transport path of the containers, between the first external application device and the internal application device is arranged a pitch change device which changes the distance between two containers succeeding each other along the transport path, wherein in a region in which sterilisation of the outer wall takes place, a distance between two containers succeeding each other along the transport path is shorter than in a region in which sterilisation of the inner wall takes place.

14. The method according to claim 13, wherein preforms are sterilised, in particular preforms for drinks containers and/or other fluid media.

15. The method according to claim 13, wherein the container is transported along a transport path which is curved at least in a segment in which is arranged the external application device for sterilising at least a segment of an outer wall of containers.

16. The apparatus according to claim 1, wherein in a region in which sterilisation of the outer surface takes place, a distance between two containers succeeding each other along the transport path is <10 cm.

17. The apparatus according to claim 1, wherein in a region in which sterilisation of the inner surface takes place, a distance between two containers succeeding each other along the transport path is >5 cm.

18. The apparatus according to claim 1, wherein in a region in which sterilisation of the outer surface takes place, the speed of the individual containers along the transport path is reduced with respect to the region in which sterilisation of the inner surface takes place.

19. The apparatus according to claim 1, wherein in a region in which sterilisation of the outer surface takes place, the number of containers transported per time interval is the same as in the region in which sterilisation of the inner surface takes place.

* * * * *